United States Patent [19]  
Davidson

[11] Patent Number: 4,814,482  
[45] Date of Patent: Mar. 21, 1989

[54] TRIFLUOROMETHYLATION PROCESS

[75] Inventor: Robert I. Davidson, Baton Rouge, La.

[73] Assignee: Ethyl Corporation, Richmond, Va.

[21] Appl. No.: 854,084

[22] Filed: Apr. 21, 1986

[51] Int. Cl.$^4$ .................... C07C 120/00; C07C 51/00; C07C 21/24
[52] U.S. Cl. .................... 558/378; 560/100; 570/144
[58] Field of Search ................ 558/423, 378; 560/100; 570/144

[56] References Cited

U.S. PATENT DOCUMENTS 4,439,617  3/1984  Sestanj et al. .................. 558/414

OTHER PUBLICATIONS

Matsui et al., "Chem. Letters," (1981), pp. 1719–1720 (Chemistry Society of Japan).

Primary Examiner—Anton H. Sutto  
Attorney, Agent, or Firm—Patricia J. Hogan

[57] ABSTRACT

Trifluoromethylaromatic compounds are prepared by reacting the corresponding aromatic bromide or iodide with potassium trifluoroacetate in the presence of cuprous iodide, a phase transfer agent, and a dipolar aprotic solvent.

20 Claims, No Drawings

TRIFLUOROMETHYLATION PROCESS

FIELD OF INVENTION

This invention relates to trifluoromethylaromatic compounds and more particularly to a process for preparing them.

BACKGROUND

As disclosed in Matsui et al., *Chemistry Letters*, 1981, pp. 1719–1720, it is known that aromatic iodides can be trifluoromethylated by reacting them with a large excess of sodium trifluoroacetate in the presence of cuprous iodide and a dipolar aprotic solvent. Matsui et al. also show that some trifluoromethylation occurs when an aromatic bromide is employed in the reaction instead of an iodide but that the yield of product is quite low.

Copending application, Ser. No. 724,474 (Ramachandran et al.), filed April 18, 1985, now U.S. Pat. No. 4,590,010, teaches that the technique of Matsui et al. is applicable to the trifluoromethylation of 6-alkoxy-5-halo-1-cyanonaphthalenes and the corresponding naphthoate esters—compounds which, like the compounds of Matsui et al., give better yields of the desired products when the halo substituent is iodo. Ramachandran et al. indicate that other trifluoroacetate salts can be used in their process, but they disclose a preference for using sodium trifluoroacetate as the trifluoromethylating agent.

Copending application Ser. No. 808,304 (Lin et al.), filed Dec. 12, 1985, teaches that potassium trifluoroacetate is more selective that sodium trifluoroacetate, can be used in smaller amounts, and does not require as long a reaction time when it is used to trifluoromethylate an aromatic bromide or iodide. Moreover, in contrast to the known processes utilizing the sodium salt, trifluoromethylations using the potassium salt can permit the products to be obtained in high yields even when the starting materials are aromatic bromides.

SUMMARY OF INVENTION

An object of this invention is to provide a novel process for preparing trifluoromethylaromatic compounds.

Another object is to increase the conversion to trifluoromethylaromatic compound obtained when an aromatic bromide or iodide is trifluoromethylated with potassium trifluoroacetate.

These and other objects are attained by reacting an aromatic bromide or iodide with potassium trifluoroacetate in the presence of cuprous iodide, a phase transfer agent, and a dipolar aprotic solvent.

DETAILED DESCRIPTION

Aromatic halides utilizable in the practice of the invention are substituted and unsubstituted aromatic iodides and bromides wherein any substituents are inert substituents (i.e., substituents that do not prevent the reaction from occurring) such as alkyl, alkoxy, alkylthio, aryl, aryloxy, arylthio, cyano, nitro, acylamino, alkylamino, tertiary amino, sulfonamido, sulfone, sulfonyl, phosphino, perfluoroalkyl, chloro, fluoro, ester, aldehyde, ketone, acetal, sulfono groups, etc., and the aromatic ring may be a carbocyclic ring such as a benzene, naphthalene, anthracene, etc., ring or a five- or six-membered heterocyclic ring having aromatic character, e.g., a pyridine, quinoline, isoquinoline, thiophene, pyrrole, furan, etc., ring. Exemplary of such compounds are iodobenzene, 3-iodotoluene, 4-chloroiodobenzene, 4-iodomethoxybenzene, 1-iodonaphthalene, 3-iodoaniline, 1-iodo-3-nitrobenzene, 2-iodothiophene, 4-iodoisoquinoline, 2-iodopyridine, 3-iodoquinoline, the corresponding bromides, etc.

In a preferred embodiment of the inventon, the aromatic halide is a halonaphthalene corresponding to the formula:

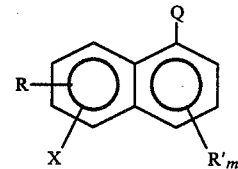

wherein R and R' are independently selected from chloro, fluoro, nitro, hydroxy, and alkyl and alkoxy substituents containing 1–6 carbons; Q is —CN or —COOR''; R'' is saturated hydrocarbyl; X is bromo or iodo; and m is 0 or 1.

The halocyanonaphthalenes and halonaphthoates utilizable in the practice of the invention may be any compounds corresponding to the above halonaphthalene formula, but they are preferably compounds wherein m is 0, X is in the 5-position, and R is an alkyl or alkoxy substituent in the 6-position. When the R and R' substituents are alkyl or alkoxy, they are generally straightchain groups of 1–3 carbons or branched-chain groups of three or four carbons, such as methyl, ethyl, propyl, 1-methylethyl, butyl, 2-methylpropyl, 1,1-dimethylethyl, the corresponding alkoxy groups, etc., although, as indicated above, larger groups such as hexyl and hexoxy are also utilizable. When the halonaphthalene is an ester, R'' may be any saturated hydrocarbyl group (i.e., a hydrocarbyl group that is free of aliphatic unsaturation) but is preferably an alkyl, cycloalkyl, aryl, alkaryl, or aralkyl group containing 1–10 carbons, e.g., methyl, ethyl, propyl, cyclohexyl, phenyl, tolyl, benzyl, etc. Particularly preferred halonaphthalenes are 6-alkoxy-5-bromo-1-cyanonaphthalenes, 6-alkoxy-5-iodo-1-cyanonaphthalenes, 6-alkoxy-5-bromo-1-naphthoates, and 6-alkoxy-5-iodo-1-naphthoates, especially those compounds wherein the alkoxy groups are methoxy.

The halonaphthoates are known compounds. The halocyanonaphthalenes are compounds that can be prepared by cyanating the appropriately substituted tetralone, e.g., 6-methoxytetralone, to form the appropriately substituted 1-cyano-3,4-dihydronaphthalene, e.g., 6-methoxy-1-cyano-3,4-dihydronaphthalene, aromatizing the product in any suitable manner, and brominating or iodinating the resultant substituted 1-cyanonaphthalne by known techniques.

The amount of potassium trifluoroacetate reacted with the aromatic halide is not critical and may be a considerable excess, such as the amounts of sodium trifluoroacetate that have been employed in the past. However, since such large amounts of potassium trifluoroacetate are not required, the amount used is generally in the range of about 1–3 equivalents, most commonly about 1.5–2 equivalents.

The phase transfer agent may be any such agent but is generally a tetraalkylammonium or tetralkylphosphonium halide, preferably a bromide or iodide. In these compounds the alkyl groups may be the same or different, straight-chain or branched, and contain about 1–20 carbons, usually about 1–12 carbons. Exemplary of such compounds are the tetramethyl, tetraethyl, tetrapropyl, tetrabutyl, tetrapentyl, tetrahexyl, tetraheptyl, methyltributyl, methyltrioctyl, methyltrialkyl($C_8$-$C_{10}$), butyltripropyl, heptyltriethyl, octyltriethyl, dodecyltrimethyl, dodecyltriethyl, tetradecyltrimethyl, and hexadecyltrimethylammonium bromides, the corresponding iodides, the corresponding phosphonium halides, etc. The preferred phase transfer agents are the halides in which the alkyl groups contain about 1–6 carbon atoms, especially tetramethylammonium bromide. The amount of phase transfer agent employed does not appear to be critical but is conveniently in the range of about 0.01–1, generally about 0.1–0.3, equivalent.

Dipolar aprotic solvents that may be utilized include, e.g., N-methylpyrrolidone, N,N-dimethylformamide, N,N-dimethylacetamide, hexamethylphosphoric triamide, dimethylsulfoxide, etc. The particular solvent employed does not appear to be critical except in the sense that it should have an appropriate boiling point for use at the reaction temperatures to be utilized, but the preferred solvents are N,N-dimethylformamide and N,N-dimethylacetamide. The solvent is used in solvent amounts, e.g., an amount such as to provide an organic solids concentration of up to about 15%.

The cuprous iodide may be employed in any suitable amount, generally an amount in the range of about 0.5–5 equivalents. lents.

The reaction is conducted by combining the ingredients in any convenient order and heating them at a suitable temperature, conveniently reflux temperature, to accomplish the desired trifluoromethylation. Anhydrous conditions are preferably employed, and the temperature is generally in the range of about 130°–160° C., preferably about 140°–155° C.

After completion of the reaction, the product may be recovered by conventional techniques and/or subjected to further reactions to form derivatives. For example, products obtained by trifluoromethylating the preferred halocyanonaphthalenes and halonaphthoates can be subjected to reactions such as those taught by Sestanj et al. in U.S. Pat. No. 4,439,617. Thus, e.g., (1) a (trifluoromethyl)cyanonaphthalene or trifluoromethylnaphthoate prepared by the trifluoromethylation reaction may be hydrolyzed to the corresponding acid in the presence of a base such as sodium or potassium hydroxide, (2) the acid can be halogenated, e.g., by reaction with thionyl chloride, to form the corresponding acid halide, (2) the acid halide may be reacted with a saturated hydrocarbyl ester of an acid corresponding to the formula $ZNHCH_2COOH$ (e.g., methyl, ethyl, propyl, cyclohexyl, phenyl, tolyl, or benzyl sarcosinate, the corresponding esters of aminoacetic acids having other N-substituents containing 1–6 carbons, such as N-ethyl, N-propyl, etc.) to form an amide corresponding to the formula:

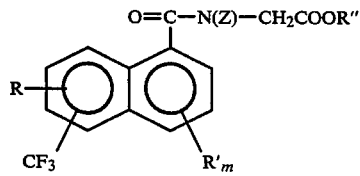

and (3) the amide maybe thiated, e.g., with phosphorus pentasulfide or the like, and the product saponified and hydrolyzed to form a thioamide corresponding to the formula:

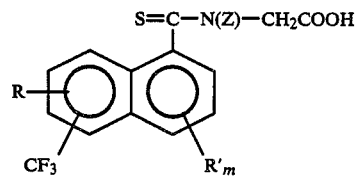

The invention is advantageous in that it permits trifluoromethylaromatic compounds to be prepared in high yields from the corresponding aromatic bromides or iodides at a faster rate, with greater selectivity, and with the use of less reagent than is required when sodium trifluoroacetate is employed. Also, it leads to the attainment of higher conversions than are obtained when potassium trifluoroacetate is used in the absence of a phase transfer agent.

The following examples are given to illustrate the invention and are not intended as a limitation thereof.

EXAMPLE

A mixture of one molar proportion of 6-methoxy-5-bromo-1-cyanonaphthalene (MBCN), 1.5 molar proportions of potassium trifluoroacetate, 2.1 molar proportions of CuI, and 0.1 molar proportion of tetramethylammonium bromide was stirred into 18 molar proportions of toluene, after which part of the toluene was stripped, 80 molar proportions of N,N-dimethylformamide (DMF) were added, and toluene and DMF were stripped until the temperature reached about 155° C. The reaction mixture was maintained at about 155° C. for four hours, cooled, worked up, and subjected to HPLC analysis. The analysis showed 88.1% by weight of 6-methoxy-5-trifluoromethyl-1-cyanonaphthalene (MTCN) and only 1.2% by weight of unreacted MBCN.

COMPARATIVE EXAMPLE

The above example was essentially repeated except that the tetramethylammonium bromide was not employed. The analysis of the product showed 88.0% by weight of MTCN and 4.7% by weight of unreacted MBCN.

It is obvious that many variations may be made in the products and processes set forth above without departing from the spirit and scope of this invention.

What is claimed is:

1. In a process for preparing a trifluoromethylaromatic compound by reacting an aromatic bromide or iodide with potassium trifluoroacetate in the presence of cuprous iodide and a dipolar aprotic solvent at a temperature of about 130°–160° C., the improvement which comprises conducting the reaction in the presence of a phase transfer agent.

2. The process of claim 1 wherein the aromatic halide is a bromide.

3. The process of claim 1 wherein the aromatic halide is an iodide.

4. The process of claim 1 wherein the aromatic halide is a halonaphthalene corresponding to the formula:

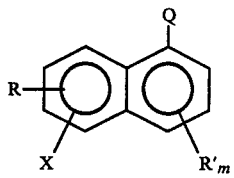

wherein R and R' are independently selected from chloro, fluoro, nitro, hydroxy, and alkyl and alkoxy substituents containing 1-6 carbons; Q is —CN or —COOR''; R'' is saturated hydrocarbyl; X is bromo or iodo; and m is 0 or 1.

5. The process of claim 4 wherein the aromatic halide is a 6-alkoxy-5-bromo-1-cyanonaphthalene.

6. The process of claim 4 wherein the aromatic halide is a 6-alkoxy-5-bromo-1-naphthoate.

7. The process of claim 1 wherein the phase transfer agent is a tetraalkylammonium or phosphonium halide.

8. The process of claim 7 wherein the phase transfer agent is a tetraalkylammonium bromide or iodide in which the alkyl groups contain 1-20 carbons.

9. The process of claim 8 wherein the alkyl groups contain 1-12 carbons.

10. The process of claim 9 wherein the alkyl groups contain 1-6 carbons.

11. The process of claim 10 wherein the phase transfer agent is tetramethylammonium bromide.

12. The process of claim 1 wherein the reaction is conducted in the presence of about 0.01-1 equivalent of the phase transfer agent.

13. The process of claim 1 wherein the reaction is conducted at about 140°-155° C.

14. The process of claim 1 wherein the aromatic halide is reacted with about 1-3 equivalents of potassium trifluoroacetate.

15. The process of claim 1 wherein the solvent is N,N-dimethylformamide.

16. The process of claim 1 wherein the solvent is N,N-dimethylacetamide.

17. A process which comprises reacting a halonaphthalene corresponding to the formula:

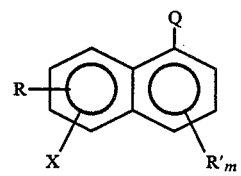

wherein R and R' are independently selected from chloro, fluoro, nitro, hydroxy, and alkyl and alkoxy substituents containing 1-6 carbons; Q is —CN or —COOR''; R'' is saturated hydrocarbyl; X is bromo or iodo; and m is 0 or 1, with about 1-3 equivalents of potassium trifluoroacetate in the presence of a dipolar aprotic solvent, about 0.1-0.3 equivalent of a tetraalkylammonium or phosphonium halide phase transfer agent, and about 0.5-5 equivalents of cuprous iodide at about 140°-155° C. so as to form a trifluoromethylaromatic compound.

18. The process of claim 17 wherein the halonaphthalene is a 6-alkoxy-5-bromo-1-cyanonaphthalene.

19. The process of claim 17 wherein the halonaphthalene is a 6-alkoxy-5-bromo-1-naphthoate.

20. The process of claim 17 wherein the phase transfer agent is a tetraalkylammonium bromide or iodide in which the alkyl groups contain 1-6 carbons.

* * * * *